(12) United States Patent
Barker et al.

(10) Patent No.: US 8,309,517 B2
(45) Date of Patent: Nov. 13, 2012

(54) LGI, LINGO AND P75NTR FAMILY MEMBERS: NOVEL MODULATORS OF NEURONAL GROWTH

(75) Inventors: Philip A. Barker, Beaconsfield (CA); Alyson Fournier, Montreal (CA); Jose Manuel Morante Redolat, Jaume Rolg (ES); Jordi Perez-Tur, Jaume Rolg (ES)

(73) Assignee: McGill University, Montreal (CA)

( * ) Notice: Subject to any disclaimer, the term of this patent is extended or adjusted under 35 U.S.C. 154(b) by 757 days.

(21) Appl. No.: 11/920,522

(22) PCT Filed: May 16, 2006

(86) PCT No.: PCT/CA2006/000795
§ 371 (c)(1),
(2), (4) Date: Apr. 22, 2009

(87) PCT Pub. No.: WO2006/136006
PCT Pub. Date: Dec. 28, 2006

(65) Prior Publication Data
US 2009/0221479 A1    Sep. 3, 2009

Related U.S. Application Data

(60) Provisional application No. 60/681,175, filed on May 16, 2005, provisional application No. 60/752,411, filed on Dec. 22, 2005.

(51) Int. Cl.
*A61K 38/00* (2006.01)
(52) U.S. Cl. .................. 514/8.3; 514/16.5; 514/17.7
(58) Field of Classification Search .................. None
See application file for complete search history.

(56) References Cited

OTHER PUBLICATIONS

Krex et al., 202, Acta Neuropathol., 103, pp. 255-266.*
Kunapuli et al., 2003, Oncogene, 22, 3985-91.*

* cited by examiner

*Primary Examiner* — Olga N Chernyshev
(74) *Attorney, Agent, or Firm* — Norton Rose Canada LLP (57) ABSTRACT

The present invention relates to a novel method to promote regeneration or repair of the central or peripheral nervous system following injury The present invention concerns the use of a leucine-rich, glioma-inactivated protein (LGIn), or an analog or derivative thereof, to promote the regeneration or remyelination of neurons after injury to the central nervous system LGIns are endogenous proteins secreted by central neurons that promote regeneration of neurons after injury to the central nervous system The present invention includes an assay to measure the interaction of LGIn with LINGOn and p75NTRn as well as to identify factors that enhance or disrupt these interactions The invention further includes cell lines capable of expressing LGIn, LINGOn and p75NTRn molecules, as well as the proteins purified from these cells.

5 Claims, 6 Drawing Sheets

```
mLGI1   1  MESESSRRMGNACIPLKRIAYFLCLFSVVLLTEGKKPAKPKCPAVCTCSKDNALCENARS
rLGI1   1  MESESIRRMGNACIPLKRIAYFLCLFSVVLLTEGKKPAKPKCPAVCTCSKDNALCENARS
hLGI1   1  MESERSKRMGNACIPLKRIAYFLCLSAILLTEGKKPAKPKCPAVCTCTKDNALCENARS mLGI1  61  IPRTVPPDVISLSFVRSGFTEISEGSFLFTPSLQLLLFTSNSFDVISDDAFIGLPHLEYI
rLGI1  61  IPRTVPPDVISLSFVRSGFTEISEGSFLFTPSLQLLLFTSNSFDVISDDAFIGLPHLEYI
hLGI1  61  IPRTVPPDVISLSFVRSGFTEISEGSFLFTPSLQLLLFTSNSFDVISDDAFIGLPHLEYI mLGI1 121  FIENNNIKSISRHTFRGLKSLIHLSLANNNLQTIPKDIFKGLDSLTNVDLRGNAFNCDCK
rLGI1 121  FIENNNIKSISRHTFRGLKSLIHLSLANNNLQTIPKDIFKGLDSLTNVDLRGNSFNCDCK
hLGI1 121  FIENNNIKSISRHTFRGLKSLIHLSLANNNLQTIPKDIFKGLDSLTNVDLRGNSFNCDCK mLGI1 181  LKWLVEWLGHTNATVEDIYCEGPPEYKKRKINSLSPKDFDCIITEFAKSQDLPYQSLSID
rLGI1 181  LKWLVEWLGHTNATVEDIYCEGPPEYKKRKINSLSPKDFDCIITEFAKSQDLPYQSLSID
hLGI1 181  LKWLVEWLGHTNATVEDIYCEGPPEYKKRKINSLSSKDFDCIITEFAKSQDLPYQSLSID mLGI1 241  TFSYLNDEYVVIAQPFTGKCIFLEWDHVEKTFRNYDNITGTSTVVCKPIVIDTQLYVIVA
rLGI1 241  TFSYLNDEYVVIAQPFTGKCIFLEWDHVEKTFRNYDNITGTSTVVCKPIVIDTQLYVIVA
hLGI1 241  TFSYLNDEYVVIAQPFTGKCIFLEWDHVEKTFRNYDNITGTSTVVCKPIVIETQLYVIVA mLGI1 301  QLFGGSHIYKRDGFANKFIKIQDIEVLKIRKPNDIETFKIEDNWYFVVADSSKAGFTTIY
rLGI1 301  QLFGGSHIYKRDGFANKFIKIQDIEVLKIRKPNDIETFKIEDNWYFVVADSSKAGFTTIY
hLGI1 301  QLFGGSHIYKRDSFANKFIKIQDIEILKIRKPNDIETFKIENNWYFVVADSSKAGFTTIY mLGI1 361  KWNGNGFYSHQSLHAWYRDTDVEYLETARPPIALRTPHLILSSSSQRPVIYQWSKATQLF
rLGI1 361  KWNGNGFYSHQSLHAWYRDTDVEYLETARPPLTIRTPHLILSSSSQRPVIYQWSKATQLF
hLGI1 361  KWNGNGFYSHQSLHAWYRDTDVEYLEIVBTQTLRTPHLILSSSSQRPVIYQWNKATQLF mLGI1 421  TNQTDIPNMEDVYAVKHFSVKGDVYICLTRFIGDSKVMKWGGSSFQDIQRMPSRGSMVFQ
rLGI1 421  INQTDIPNMEDVYAVKHFSVKGDVYICLTRFIGDSKVMKWGGSSFQDIQRMPSRGSMVFQ
hLGI1 421  TNQTDIPNMEDVYAVKHFSVKGDVYICLTRFIGDSKVMKWGGSSFQDIQRMPSRGSMVFQ mLGI1 481  PLQINNYQYAILGSDYSFTQVYNWDAEKAKFVKFQELNVQAPRSFTHVSINKRNFLFASS
rLGI1 481  PLQINNYQYAILGSDYSFTQVYNWDAEKAKFVKFQELNVQAPRSFTHVSINKRNFLFASS
hLGI1 481  PLQINNYQYAILGSDYSFTQVYNWDAEKAKFVKFQELNVQAPRSFTHVSINKRNFLFASS mLGI1 541  FKGNTQIYKHVIVDLSA (SED ID NO : 1)
rLGI1 541  FKGNTQIYKHVIVDLSA (SEQ ID NO : 2)
hLGI1 541  FKGNTQIYKHVIVDLSA (SEQ ID NO : 3)
```

LGI, LINGO AND P75NTR FAMILY MEMBERS: NOVEL MODULATORS OF NEURONAL GROWTH

CROSS-REFERENCE TO RELATED APPLICATIONS

This application claims the benefit of U.S. Provisional Application No. 60/681,175 filed on May 16, 2005, and of U.S. Provisional Application No. 60/752,411 filed on Dec. 22, 2005, both of which are hereby incorporated by reference in their entirety.

FIELD OF THE INVENTION

The present invention relates to a novel application in the field of neurobiology. Specifically, the present invention concerns the use of a leucine-rich, glioma-inactivated protein (LGIn), or an analog or derivative thereof, to promote the regeneration or remyelination of neurons after injury to the central or peripheral nervous system.

The present invention is based on the interaction of LGIn with two types of cell surface proteins, termed LINGO receptors (LINGOn) and p75 neurotrophin receptors (p75NTRn), and on their ability to promote the proliferation and differentiation of myelin producing cells in the peripheral and central nervous systems. More specifically, the present invention relates to LGIn, including analogs and derivatives thereof, that will block, enhance or otherwise modulate these interactions, and includes the use of LGIn to enhance the proliferation and differentiation of myelin producing cells in the central and peripheral nervous systems.

BACKGROUND OF THE INVENTION

Axons in the Central Nervous System Fail to Regenerate

During development, axons extend from neuronal cell bodies towards target tissues that they will ultimately innervate. The extending tip of these nerve fibers contain a specialized structure, the growth cone, which allows the growing neuron to sense and respond to various cues along its path. Once contact is made with its target, the growth cone disappears and synaptic connections begin to form. This process repeats itself several trillion times in development to produce the mature mammalian central nervous system (CNS) that includes the brain and spinal cord.

In the adult, traumatic injury and diseases can lead to axonal damage and/or axonal severing and thus cause loss of functional connections. Typically, the nerve fiber distal to the damage degenerates whereas the proximal segment, which is still attached to the cell body, mounts a regenerative response that involves elaboration of a growth cone that attempts to re-grow toward its target. In the peripheral nervous system, this rewiring can be quite successful and often leads to full or partial recovery of function. However, in the central nervous system, this regenerative process almost invariably fails, resulting in the permanent paralysis and sensory loss seen, for example, after spinal cord injury.

Over the last three decades, factors that contribute to regenerative failure in the CNS have been identified. A series of landmark studies by Albert Aguayo and Sam David set the stage for this work by demonstrating that lesioned CNS neurons will readily grow into peripheral nerves grafted into the site of injury (1, 2). The hypothesis that injured CNS neurons are capable of regenerating if provided with an appropriate environment led many labs to begin to search for environmental cues that alter growth of injured central neurons. The paradigm that has emerged from these combined efforts is that the adult central nervous system contains inhibitory factors that actively block neuronal growth (3). Notably, several factors present in central nervous system myelin have emerged as potent inhibitors of axonal growth. There is now a general consensus that blocking the actions of these myelin-based axon growth inhibitors (MBGIs) will enhance the ability of CNS neurons to appropriately regenerate in vivo (4).

Neuronal Growth Inhibition is Mediated by Specific Ligands and Receptors

Three MBGIs, termed Nogo-A, myelin associated glycoprotein (MAG) and oligodendrocyte myelin glycoprotein (OMgp) have thus far been identified. All three of these molecules have potent neurite growth inhibitory effects in vitro (reviewed in (3)). Considerable attention has focused on Nogo-A because in vivo delivery of antibodies directed against this protein can stimulate regeneration and functional recovery in animal models of spinal cord trauma (5-8). Mice null for Nogo-A and MAG have yielded variable results, with some labs reporting a slight effect and others reporting none at all (9, 10). The reasons for the limited effects seen in these null mice are not entirely clear at present, nevertheless, there is strong evidence based on numerous studies that (i) Nogo-A and MAG can cause collapse of the growth cone and arrest of nerve fiber growth in vitro and (ii) blocking Nogo-A or all of the MBGI activities with antibodies promotes extensive long distance axon regeneration after spinal cord injuries (7, 8, 11). The consensus in the field is that these MBGIs are important contributors to the failure of axon regeneration after spinal cord and other CNS damage (12).

MBGIs block regeneration by binding to the surface of neurons and inducing collapse of growth cones. The characterization of receptors for these factors was a key priority for the field, and the identification of the Nogo receptor (NgR) in 2001 by Alyson Fournier was a key breakthrough for two reasons (13). First, the NgR, which is a GPI-anchored leucine-rich repeat protein, was the first MBGI receptor identified and second, it quickly led to the discovery that MAG and OMgp, which are also ligands for the NgR (14). Thus, NgR is a common receptor for these three structurally unrelated MBGIs. Recent studies have indicated that blocking NgR with a neutralizing peptide or blocking the action of MBGIs using soluble NgR promotes growth after spinal cord injury, underlining the crucial role for the MBGI-NgR complex in neuronal growth inhibition in vivo (15, 16).

MBGI Receptor Complexes

NgR is a not a transmembrane protein but rather is attached to the membrane via a GPI-linkage (13). This suggests that other transmembrane components capable of transducing intracellular signals are likely to be part of an MBGI receptor complex. Activation of RhoA, an intracellular GTPase, plays a crucial role in the growth inhibitory effect of MBGIs, and therefore, neuronal receptors that act as Rho activators are potential components of this complex. The discovery that p75 neurotrophin receptor (p75NTR) activates RhoA (17) prompted studies to determine if p75NTR plays a role in MBGI-induced growth inhibition. Consistent with this, Yamashita and colleagues found that MAG-induced growth inhibition and RhoA activation are reduced in neurons (CGNs) derived from p75NTR null mice (18) and others showed that p75NTR forms a complex with NgR on the cell surface (19, 20). Recently, a transmembrane leucine-rich repeat protein termed LINGO1 has been identified as an additional component of the MBGI receptor complex (21).

Importantly, the extracellular domain of LINGO1 binds both NgR and p75NTR and in vitro studies have indicated that these three receptors collaborate to induce RhoA activation in response to MAG (18).

Thus, the MBGI receptor complex best characterized to date consists of NgR, p75NTR and LINGO1. Interestingly, emerging data suggests that other MBGI complexes may also exist. Two homologs of NgR (NgR2 and NgR3) that are similar in structure to NgR are expressed in mammals (22) and NgR2 has recently been shown to have higher affinity for MAG than NgR itself (23). p75NTR also has two close homologs, termed TROY and NRH2, and recent studies have revealed that TROY can substitute for p75NTR in the MBGI receptor complex (24, 25). The function of NRH2 is not yet clear but is presently under intense investigation. LINGO1 is a member of a family of 4 proteins (others are LINGO2, -3 and -4); all are very similar to LINGO1 and it seems likely that they may substitute for LINGO1 in an MBGI complex (21). Thus, there may be several similar MBGI receptor complexes that have complementary activities. This may explain why mice rendered null for only one of these components show little or no deficit in MBGI responses in vivo. Considering these multiple receptors will be an important consideration when developing therapeutic approaches designed to enhance neuronal growth by inhibiting MBGI receptor activation.

LGI1—An Endogenous MBGI Inhibitor

The loss of 1 copy of chromosome 10 is a common event in high-grade gliomas; in ~80% of cases where this occurs, the second copy of chromosome 10 shows some type of rearrangement or deletion (26). In 1998, Chernova and colleagues isolated a gene, termed LGI1 (for leucine-rich, glioma-inactivated-1), that was rearranged on chromosome 10 in the T98G and A172 glioma cell lines and suggested that LGI1 may be a tumor suppressor gene involved in the malignant progression of glial tumors (27). However, two studies that have directly addressed the role of LGI1 as a tumor suppressor by examining the effect of LGI1 overexpression in glioma cell lines that lack endogenous LGI1 have found opposite results; one reported no effect on growth rate, migration or DNA content (28) whereas the other reported that LGI1 reduced cell proliferation and blocked cell migration (29).

More recently, two groups have shown that mutations in the LGI1 gene are responsible for a relatively rare form of epilepsy termed autosomal dominant partial epilepsy with auditory features (ADPEAF) (30-32). Numerous truncation and point mutations in LGI1 that cause ADPEAF have now been identified, suggesting that LGI1 normally plays some role in neuronal development or maintenance (33-39). Consistent with this, in situ hybridization and immunocytochemical analyses have revealed that expression of LGI1 is predominantly neuronal (30-32). Interestingly, patients with ADPEAF that have mutations in the LGI1 gene have normal lifespans and do not show increased risk of glioma or other malignancies (40). Together with well-performed in vitro studies (28), these data have cast strong doubt on the notion that LGI1 is involved in malignant tumor progression.

Demyelinating Disorders

The myelin sheath is a crucial element in neuronal function because it greatly facilitates the ability of neurons to conduct impulses and because it protects the axons from injury. In the central nervous system, the ensheathing cells are called oligodendrocytes whereas in the peripheral nervous system, myelination is performed by Schwann cells. In adults, traumatic injury or diseases, such as multiple sclerosis (MS) or the leukodystrophies, can result in demyelination, the destruction, loss or removal of the protective myelin sheath that covers axons in the central nervous system.

Multiple sclerosis is an auto-immune disease and treatment efforts have focused on modulating immunological responses to presumed foreign antigens or self-antigens. This approach has proven useful in preventing damage from occurring but does not address the problem of repairing residual damage which can have devastating consequences for patients. The consensus among MS specialists is that neurodegeneration and the failure to repair damaged CNS tissue may play a critical role in accumulating clinical disability [52].

A major goal in treating lesions in central demyelinating disorders such as MS is to promote remyelination. After a disease episode, some remyelination can occur without intervention and treatments that enhance this natural process would likely have therapeutic benefit for patients suffering demyelinating disorders [53]. Importantly, myelin sheaths that are produced after demyelinating epidodes are not made by mature oligodendrocytes that survive the insult but instead are produced from oligodendrocyte precursor cells (OPCs) present throughout the adult CNS [54-57]. After demyelination, these cells proliferate, migrate, and occupy the demyelinated area [58-60]. For remyelination to occur, the recruited OPCs must engage demyelinated axons, restoring new myelin sheaths as they differentiate into mature oligodendrocytes.

SUMMARY OF THE INVENTION

In accordance with the present invention, there is provided a novel method to promote regeneration of neurons after injury to the central nervous system. More specifically, this method comprises the use (or administration) of a leucine-rich, glioma-inactivated protein (LGIn), or an analog or a derivative thereof, to promote the regeneration of neurons after injury to the central nervous system or peripheral nervous system. The LGIn is selected from the group consisting of LGI1, LGI2, LGI3 and LGI4. One of the advantages of the method of the present invention resides in the fact that the LGIns are soluble proteins that are indigenous to mammals that can be applied directly at the site of injury.

LGIns are believed to function by (i) blocking the action of a myelin-based axon growth inhibitor (MBGI) in order to enhance the ability of neurons of the central nervous system to regenerate and (ii) inhibiting growth cone collapse induced by Nogo66 or myelin.

Experimental results reported here further suggest that a functional interaction between LGIn, LINGOn and, p75NTRn plays a crucial role in regulating the differentiation phase of oligodendrocyte precursor cells (OPCS) and that this can be exploited for clinical benefit. Consequently, in accordance with the present invention, there is further provided a novel method to promote myelination of neurons to treat demyelinating disorders of the central or peripheral nervous systems. More specifically, this method comprises the use (or administration) of a LGIn, or an analog or a derivative thereof, to bind LINGOn or p75NTRn to treat demyelinating disorders of the central or peripheral nervous systems that may result from trauma, from disease or from chemical toxins.

The LGIn is selected from the group consisting of LGI1, LGI2, LGI3 and LGI4 and the LINGOn is selected from the group consisting of LINGO1, LINGO2, LINGO3 and LINGO4. LGIns are believed to function in this context by binding to LINGOns and p75NTRns at the cell surface and modulating intracellular signaling cascades that are regulated by LINGOn and p75NTRn.

LGIns may also be effective when placed in contact with OPCs. By enhancing proliferation of OPCs, LGIns may be used to expand pools of myelin-producing cells, thereby increasing the likelihood of re-myelination.

The present invention further includes assays based on the use of a LGIn, an analog or a derivative thereof. LGIn can be used in this manner to determine growth cone collapse which has an impact on neurite outgrowth, to measure the interaction of LGIn with LINGOn and p75NTRn, to measure the interaction of LGIn with OPCs, and to identify factors that enhance or disrupt any of these interactions.

Finally, the invention includes cell lines capable of expressing LGIn, LINGOn and p75NTRn, as well as the proteins purified from these cells.

Other objects, advantages and features of the present invention will become more apparent upon reading of the following non restrictive description of preferred embodiments thereof, given by way of example only with reference to the accompanying drawings.

DESCRIPTION OF THE PREFERRED EMBODIMENTS

Definitions

Unless defined otherwise, the scientific and technological terms and nomenclature used herein have the same meaning as commonly understood by a person of ordinary skill in the art to which the present invention belongs. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Use of the singular forms "a," "an," and "the" include plural references unless the context clearly dictates otherwise. Thus, for example, reference to "a LGIn" includes a plurality of LGIns.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

Analog: A peptide that is related to a LGIn, LINGOn or p75NTRn protein but which has been modified. This modification does not, however, alter the biological activity of the interaction domain. Reasons for modifications include, but are not limited to, increasing the peptide's stability and solubility, decreasing the probability of denaturation, reducing manufacturing costs and enhancing large-scale manufacturing.

Derivative: A derivative denotes, in the context of a functional derivative of a sequence whether a nucleic acid or amino acid sequence, a molecule that retains a biological activity (either function or structural) that is substantially similar to that of the original sequence. This functional derivative or equivalent may be a natural derivative or may be prepared synthetically. Such derivatives include amino acid sequences having substitutions, deletions, or additions of one or more amino acids, as well as chemical mimics, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid generally has chemico-physical properties which are similar to that of the substituted amino acid. The similar chemico-physical properties include, similarities in charge, bulkiness, hydrophobicity, hydrophilicity and the like. The term derivative is intended to include fragments, segments, variants, analogs or chemical derivatives, including non-peptide chemical derivatives, of the subject matter of the present invention.

LGIn protein: Leucine-rich, glioma-inactivated protein. LGIns are proteins secreted by glial cells and neurons in the central nervous system that promote regeneration of neurons after injury to the central nervous system. Four members of this highly similar family of proteins have been identified to date: LGI1, LGI2, LGI3 and LGI4. The protein LGI1, LGI2, LGI3 and LGI4 referred to in this application specify the proteins described in NCBI-GenBank Flat File Release 153.0 as records NP_005088.1, NP_060646.2, NP_644807.1, and NP_644813.1, respectively. Of the four, only LGI1 has been characterized. The LGI1 gene encodes a 557 amino acid protein that is almost 100% conserved between mice, rats and humans. It consists of an NH2 signal peptide, 3.5 leucine-rich repeats (LRRs) with conserved cysteine-rich flanking sequences and an extended domain consisting of a 7-fold repeated 44-residue motif. The architecture and structural features of this latter region, termed the EAR or EPTP domain [42, 43], suggests that it is a protein interaction domain that contains a 7-bladed beta-propeller fold.

LINGOn protein: Four members of this highly similar family of receptor proteins have been identified to date: LINGO1, LINGO2, LINGO3 and LINGO4. The proteins LINGO1, LINGO2, LINGO3 and LINGO4 referred to in this application specify the human proteins described in NCBI-GenBank Flat File Release 153.0 as records NP_116197.4, XP_944870.1, CAC22713.1, and NP_001004432.1, respectively. Of the four, only LINGO1 has been characterized. LINGO1 contains 12 leucine-rich repeat (LRR) motifs flanked by N- and C-terminal capping domains, has one extracellular immunoglobulin (Ig) domain, a transmembrane domain and a short cytoplasmic tail. A canonical epidermal growth factor receptor-like tyrosine phosphorylation site has been identified in the cytoplasmic tail.

p75NTRn: The p75NTR family consists of two closely related members of the tumor necrosis factor receptor superfamily named p75NTR and TROY (also known as tumor necrosis family members 16 and 19, respectively). Each receptor contains extracellular cysteine-rich domains, a transmembrane domain and a cytoplasmic region that contains a juxtamembrane region and a death domain.

Results

Figure 1B:
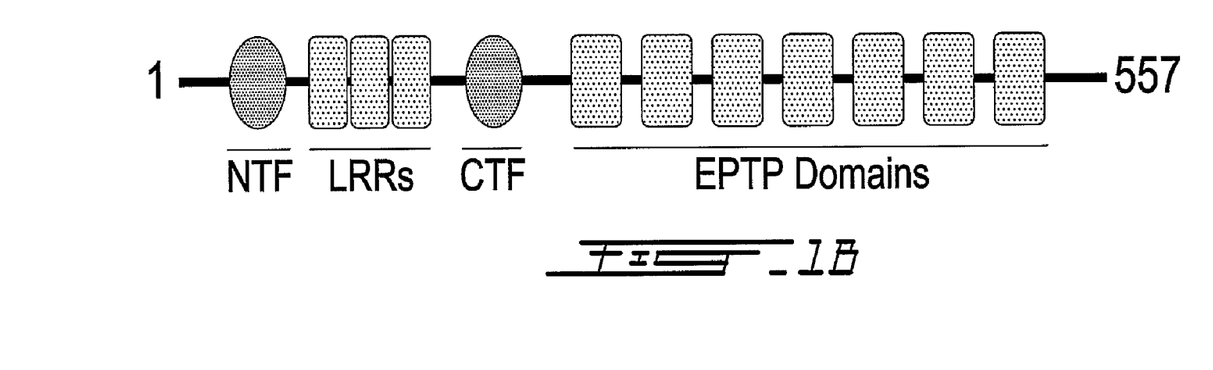
FIG. 1: The LGI1 gene encodes a 557 amino acid protein that is almost 100% conserved between mice, rats and humans.

The amino acid sequences of mouse, rat and human LGI1 (denoted mLGI1, rLGI1 and HLGI1, respectively, are shown in FIG. 1. FIG. 1(A) shows the alignment of the amino acid sequences of mouse, rat and human LGI1. Human and mouse LGI1 are 96% identical (540/557 residues). FIG. 1(B) is a schematic diagram representing domains present in LGI1 (NTF=amino terminal LRR flanking domain, CTF=carboxy terminal LRR flanking domain, LRRs=leucine-rich repeats).

Figure 2A:
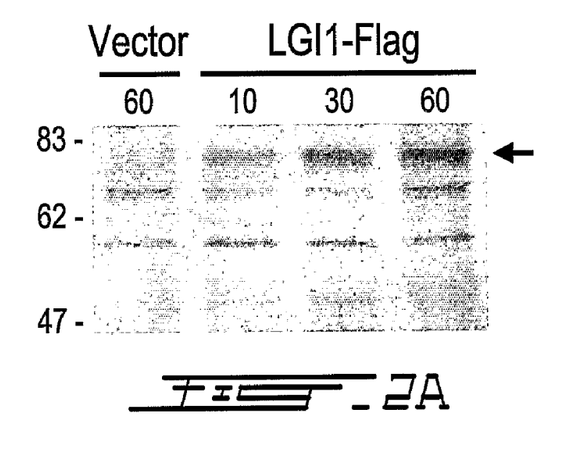
FIG. 2: Evidence showing that pulse labeled LGI1 quickly exits cells and accumulates in conditioned media.
Figure 2B:
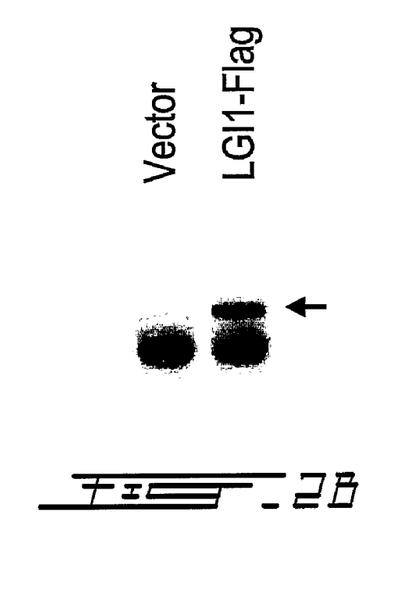

FIG. 2 provides evidence that LGI1 is a secreted protein. HEK293 cells were transfected with a plasmid encoding LGI1-FLAG or a control vector, incubated with $^{35}$S-Translabel (ICN) for 30 minutes, and then chased with media containing an excess of unlabelled cysteine and methionine for 10, 30 and 60 minutes, as indicated. LGI1-FLAG was immunoprecipitated using an anti-FLAG antibody and analysed by SDS-PAGE/fluorography (FIG. 2(A)). HEK293 cells were transfected with a plasmid encoding LGI1-FLAG or a control vector and allowed to condition in media for 72 hours. LGI1-FLAG was immunoprecipitated using an anti-FLAG antibody and analysed on immunoblots using anti-FLAG antibodies (FIG. 2(B)).

Figure 3A:
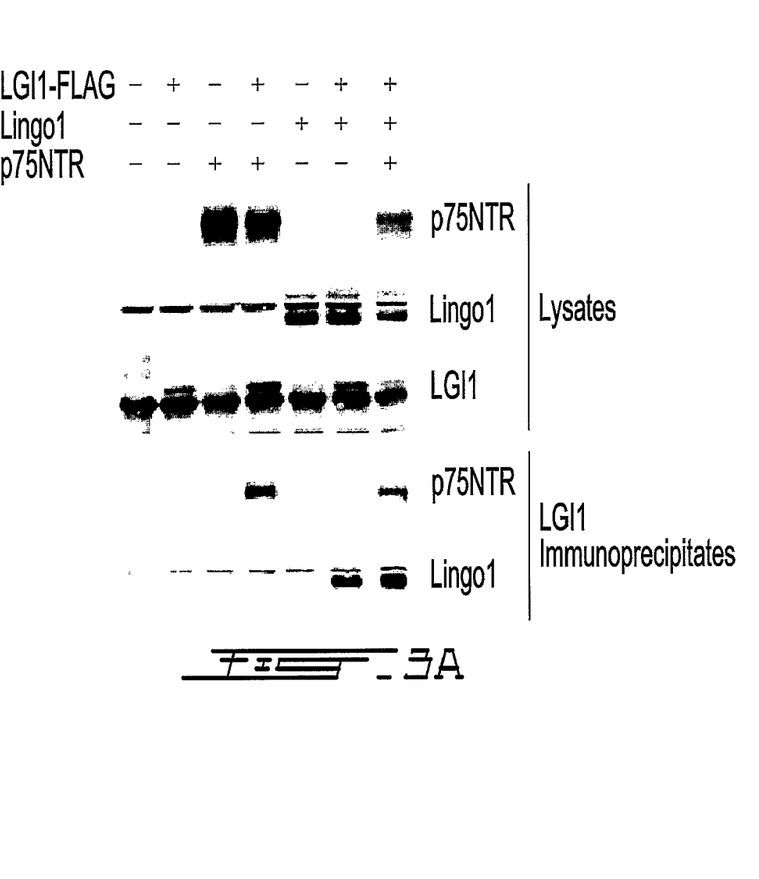
FIG. 3: Illustration showing a) that LGI1 binds to p75NTR or LINGO1, expressed alone or together, but does not bind NgR, and b) that LGI1 overexpression drastically reduces the association of p75NTR and LINGO1 with the NgR.
Figure 3B:
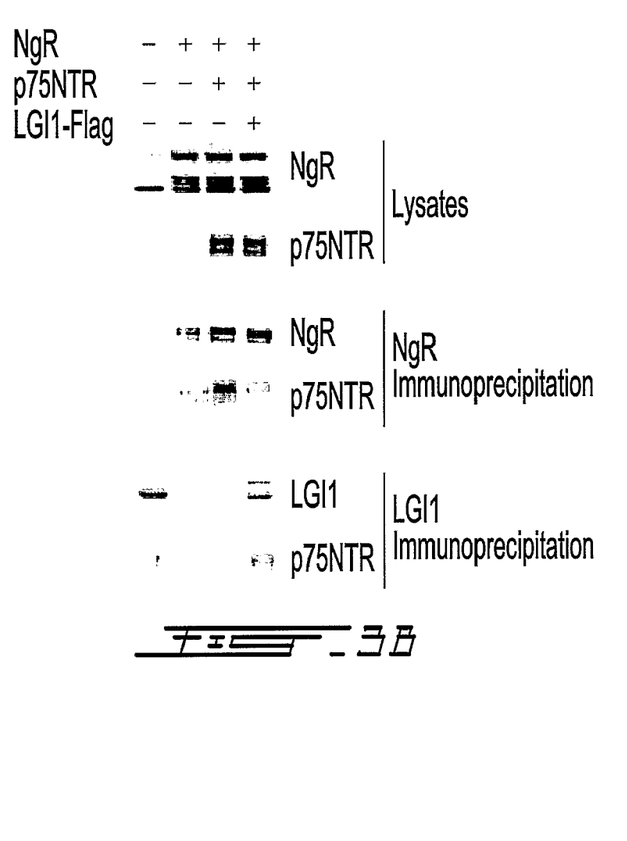

The results of FIG. 3 show that LGI1 binds 75NTR and LINGO1 and disrupts the p75NTR-NgR complex. In FIG. 3(A), HEK293 cells were transfected with plasmids encoding LGI1-FLAG, LINGO1 and/or p75NTR. Forty-eight (48) hours later, the cells were lysed and LGI1-FLAG was immunoprecipitated using an anti-FLAG antibody. Immunoprecipitates analysed by immunoblot using p75NTR and LINGO1 antibodies revealed specific co-immunoprecipitation of p75NTR and LINGO1 with LGI1-FLAG. In FIG. 3(B), HEK293 cells were transfected with plasmids encoding LGI1-FLAG, p75NTR or NgR-Myc. Forty-eight (48) hours later, the cells were lysed and immunoprecipitated using anti-Myc or anti-FLAG antibodies. Immunoprecipitates analysed by immunoblot using anti-p75NTR, anti-NgR and anti-FLAG revealed that LGI1 expression greatly reduces the association of p75NTR and NgR.

Figure 4A:
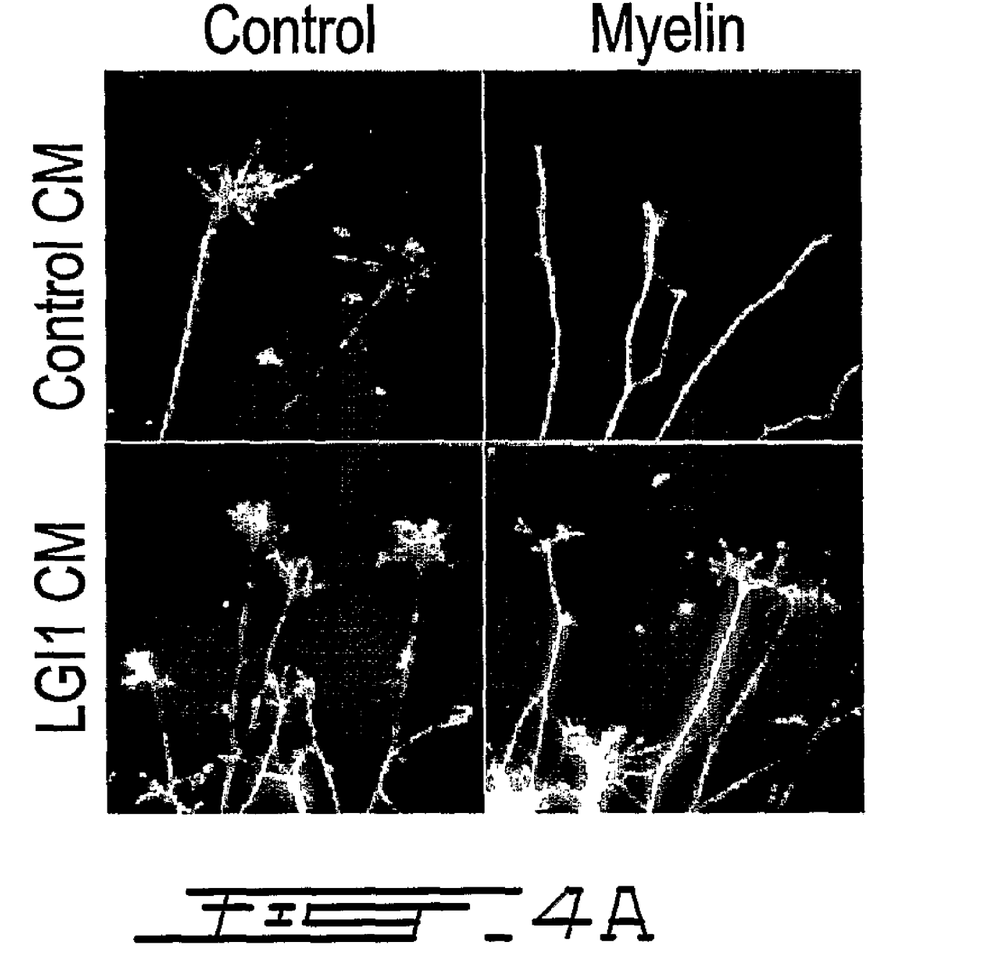
FIG. 4: Demonstration that LGI1 does indeed antagonizes the growth cone collapse activity of Nogo on primary sensory neurons.
Figure 4B:
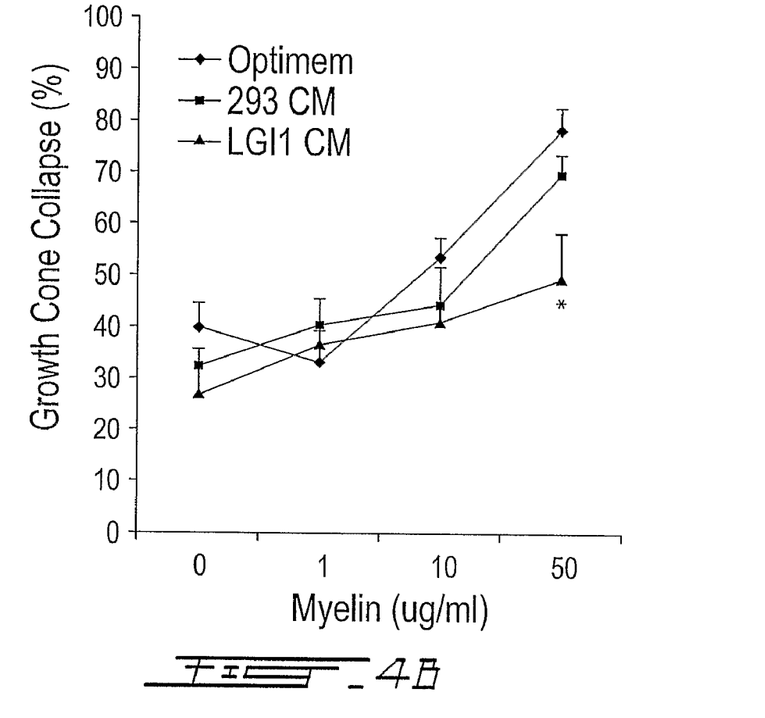

The micrographs shown in FIG. 4(A) establish that LGI1-FLAG inhibits Nogo66-induced growth-cone collapse. The incidence of growth cone collapse was quantified in Figure (B), in accordance with the method described by Y. Luo et al [46]. Briefly, growth cone collapse assays were performed on E13 chick DRG explants as described by Y. Luo et al [46] using media conditioned by HEK293 cells transfected with LGI1-FLAG (LGI1) or with parental vector (293T). A representative set of micrographs (FIG. 4(A)) shows growth cone collapse induced by myelin and the protection conferred by LGI1 conditioned media. Quantification of the growth cone collapse (FIG. 4(B)) reveals that cells treated with LGI1 conditioned media show a statistically significant reduction in growth cone collapse over controls ('*'=P<0.05).

Figure 5:
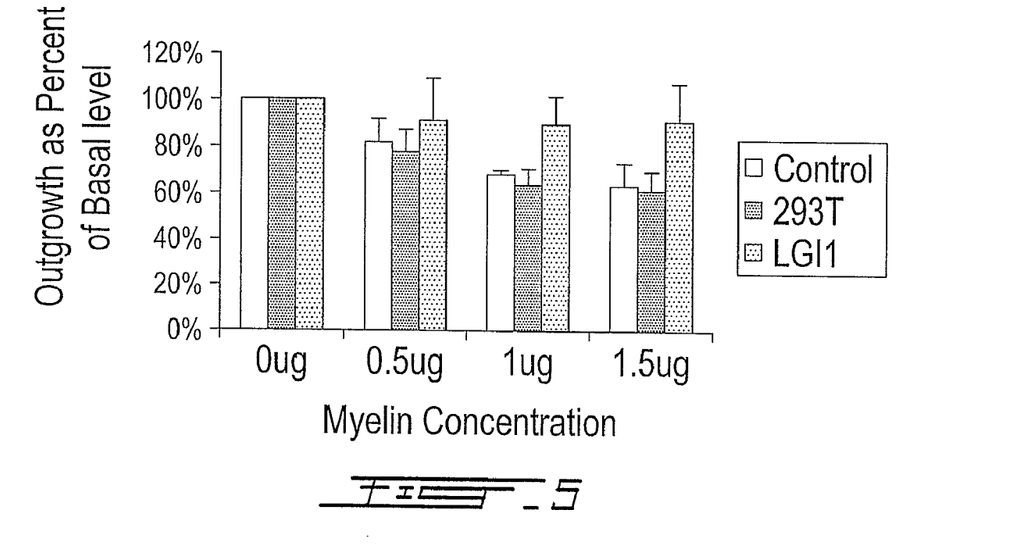
FIG. 5: Demonstration that LGI1 facilitates neurite outgrowth on inhibitory substrates.

FIG. 5 shows that LGI1-FLAG facilitates growth of central neurons plated on an inhibitory substrate. Dissociated cerebellar neurons derived from P8 rat pups were plated on increasing concentrations of myelin in the presence of media conditioned by HEK293 cells transfected with LGI1-FLAG (LGI1) or with parental vector (293T). Twenty-four (24) hours later, neurite outgrowth was quantified using NeuronJ as described by A. Fournier et al [13].

Figure 6:
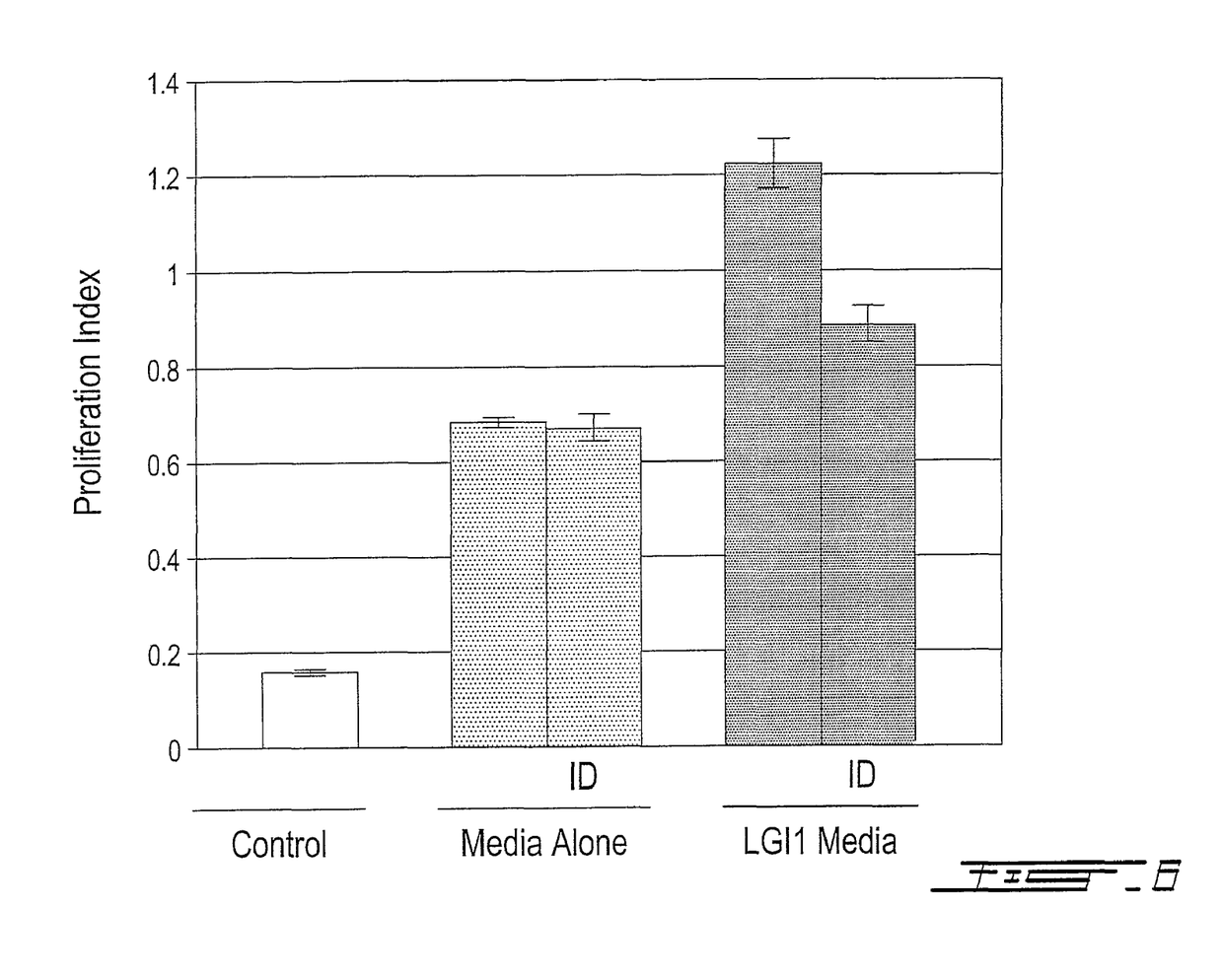
FIG. 6: Effect of LGI1 on the oligodendrocyte-derived cell line OLN93.

To begin to elucidate the function of LGI1 on oligodendrocytes, the effect of LGI1 on OLN93 cells, a rat oligodendrocyte cell line, was analysed. For this, serum-starved OLN93 cells were treated with conditioned media containing LGI1-Flag or with control conditioned media lacking LGI1-Flag. Under conditions of serum-starvation, OLN93 cells become metabolically inactive and eventually die. FIG. 6 shows that cells treated with HEK293 conditioned media show an increase in metabolic activity relative to the DMEM control, and this was increased still further using conditioned media containing LGI1-Flag. The media was provided directly or after immunodepletion with Flag-specific antibodies (ID).

To confirm that LGI1-Flag actually contributed to the proliferation effect, anti-Flag antibodies were used to remove LGI1-Flag from the conditioned media. The immunodepleted media showed a dramatic reduction in its ability to support OLN93 cells. Importantly, anti-Flag immunodepletion of control media (DMEM) had no effect.

Discussion

LRR-containing proteins are involved in cell-cell adhesion and neurite process outgrowth (43, 44) and it is hypothesized that LGI1 is a secreted protein that functions to regulate axonal growth. The following summarizes how this possibility was analyzed.

LGI1 was originally hypothesized to be a Type I membrane protein (27). It has since been established that LGI1 is actually a secreted protein by performing pulse-chase analyses on HEK293 cells transfected with a cDNA encoding LGI1-FLAG. FIG. 2 shows that pulse labeled LGI1 quickly exits cells and accumulates in conditioned media. Immunocytochemical and cell surface biotinylation analyses established that LGI1 does not accumulate on the cell surface (data not shown), consistent with the hypothesis that the protein is secreted.

LGI1 was examined to determine whether it binds NgR, p75NTR or LINGO1, the cell surface receptors that comprise MGBI receptors. For these experiments, LGI1-FLAG was co-expressed with these receptors, either alone or in combination, before attempting to co-immunoprecipitate ligand-receptor complexes using anti-FLAG antibodies. FIG. 3(A) shows that LGI1 binds to p75NTR or LINGO1, expressed alone or together, but does not bind NgR.

In a separate set of experiments, LGI1 was examined to determine whether it binds LINGO1 or p75NTR. For these experiments, LGI1-Fc was co-expressed with LINGO1 and p75NTR, either alone or in combination, before attempting to co-immunoprecipitate ligand-receptor complexes using Protein A-conjugated beads. These experiments confirmed that LGI1 specifically binds to LINGO1 and to p75NTR. The experiments also indicate that LGI1 does not bind to Robo, a distantly related LRR receptor (results not shown).

Because NgR is the MBGI-binding component of the receptor complex, these results raised the possibility that LGI1 may bind p75NTR and LINGO1, displace NgR from the MBGI complex and thereby attenuate MBGI signaling. Consistent with this, FIG. 3(B) shows that LGI1 overexpression drastically reduces the association of p75NTR and LINGO1 with the NgR.

To examine the functional consequences of LGI1 on MBGI action, experiments were devised to test whether LGI1 antagonizes the actions of Nogo. In a first set of experiments, the focus was on whether LGI1 prevents growth cone collapse induced by Nogo66 (the biologically active fragment of Nogo that binds NgR). FIG. 4 shows that LGI1 does indeed antagonize the growth cone collapse activity of Nogo on primary sensory neurons.

Primary cerebellar neurons maintained in the presence of MBGIs activate signaling pathways that inhibit growth cone extension and as a result show little or no neurite outgrowth. In one set of experiments, the focus of the investigation was on whether LGI1 can "inhibit this inhibition" and thus promote neurite growth from primary cerebellar neurons maintained in the presence of myelin. FIG. 5 demonstrates that LGI1 does indeed facilitate neurite outgrowth on inhibitory substrates.

Recent discoveries have indicated a role for LGI4 in peripheral nerve myelination and for LINGO1 in CNS myelination [25, 27]. The above results show that LGI1 specifically binds to LINGO1. Consequently, it is hypothesized that LGIn regulate myelination through interactions with LINGOn.

The above results are significant for several reasons. First, they demonstrate that LGI1 is a secreted protein and therefore likely to bind cell surface proteins. Second, they identify p75NTR and LINGO1, components of the MBGI receptor complex, as LGI1 binding partners. Third, these findings show that LGI1 acts to displace NgR from the MBGI receptor complex and to antagonize MBGI action. This is a major finding because it demonstrates that inhibitors of MBGI action are produced endogenously. This, in turn, raises the possibility that LGI1 or related molecules can be utilized therapeutically to promote neuronal growth in the damaged CNS.

The above results are also significant because they suggest that the function of LGI1 is to facilitate proliferation of oligodendrocyte precursor cells (OPCs). Myelin ensheathing cells of the CNS and PNS have to go through several developmental stages. As they migrate to their destination in the nervous system, they initially proliferate at a high rate but then drop out of the cell cycle and begin to produce myelin and extend processes the envelop the nerve sheath. It would appear that LGI1 may function by preventing the cell cycle exit of these cells, thereby 'locking' them in a proliferative phase until the appropriate stage of development. This has clinical implications since it suggests that LGI1 (and by extension, LGI2, LGI3, LGI4) may be used to expand pools of myelin-producing cells and thereby increase likelihood of re-myelination through indirect means.

While the emphasis in the above description may have been placed on the repair or regeneration of cells of the central nervous system, it is believed that members of the LGIn family would also be effective in the repair and regeneration of cells of the peripheral nervous system. Consequently, applications specific to the repair and regeneration of the peripheral nervous system are also encompassed by the scope of the present invention.

Although the present invention has been described hereinabove by way of preferred embodiments thereof, it can be modified without departing from the spirit, scope and nature of the subject invention, as defined in the appended claims.

List Of References

1. Aguayo, A. J., David, S., and Bray, G. M. Influences of the glial environment on the elongation of axons after injury: transplantation studies in adult rodents. J Exp Biol 1981; 95:231-240.
2. David, S. and Aguayo, A. J. Axonal elongation into peripheral nervous system "bridges" after central nervous system injury in adult rats. Science 1981; 214:931-933.
3. Grados-Munro, E. M. and Fournier, A. E. Myelin-associated inhibitors of axon regeneration. J Neurosci Res 2003; 74:479-485.
4. Lee, D. H., Strittmatter, S. M., and Sah, D. W. Targeting the Nogo receptor to treat central nervous system injuries. Nat Rev Drug Discov 2003; 2:872-878.
5. Brosamle, C., Huber, A. B., Fiedler, M., Skerra, A., and Schwab, M. E. Regeneration of lesioned corticospinal tract fibers in the adult rat induced by a recombinant, humanized IN-1 antibody fragment. J Neurosci 2000; 20:8061-8068.
6. Thallmair, M., Metz, G. A., Z'Graggen, W. J., Raineteau, O., Kartje, G. L., and Schwab, M. E. Neurite growth inhibitors restrict plasticity and functional recovery following corticospinal tract lesions. Nat Neurosci 1998; 1:124-131.
7. Bregman, B. S., Kunkel-Bagden, E., Schnell, L., Dai, H. N., Gao, D., and Schwab, M. E. Recovery from spinal cord injury mediated by antibodies to neurite growth inhibitors. Nature 1995; 378:498-501.
8. Schnell, L. and Schwab, M. E. Axonal regeneration in the rat spinal cord produced by an antibody against myelin-associated neurite growth inhibitors. Nature 1990; 343: 269-272.
9. Kim, J. E., Li, S., GrandPre, T., Qiu, D., and Strittmatter, S. M. Axon regeneration in young adult mice lacking Nogo-A/B. Neuron 2003; 38:187-199.
10. Zheng, B., Ho, C., Li, S., Keirstead, H., Steward, O., and Tessier-Lavigne, M. Lack of enhanced spinal regeneration in Nogo-deficient mice. Neuron 2003; 38:213-224.
11. Huang, D. W., McKerracher, L., Braun, P. E., and David, S. A therapeutic vaccine approach to stimulate axon regeneration in the adult mammalian spinal cord. Neuron 1999; 24:639-647.
12. McKerracher, L. and David, S. Easing the brakes on spinal cord repair. Nat Med 2004; 10:1052-1053.
13. Fournier, A. E., GrandPre, T., and Strittmatter, S. M. Identification of a receptor mediating Nogo-66 inhibition of axonal regeneration. Nature 2001; 409:341-346.
14. Watkins, T. A. and Barres, B. A. Nerve regeneration: regrowth stumped by shared receptor. Curr Biol 2002; 12:R654-656.
15. Li, S. and Strittmatter, S. M. Delayed systemic Nogo-66 receptor antagonist promotes recovery from spinal cord injury. J Neurosci 2003; 23:4219-4227.
16. Li, S., Liu, B. P., Budel, S., Li, M., Ji, B., Walus, L., Li, W., Jirik, A., Rabacchi, S., Choi, E., Worley, D., Sah, D. W., Pepinsky, B., Lee, D., Relton, J., and Strittmatter, S. M. Blockade of Nogo-66, myelin-associated glycoprotein, and oligodendrocyte myelin glycoprotein by soluble Nogo-66 receptor promotes axonal sprouting and recovery after spinal injury. J Neurosci 2004; 24:10511-10520.
17. Yamashita, T., Tucker, K. L., and Barde, Y. A. Neurotrophin binding to the p75 receptor modulates Rho activity and axonal outgrowth. Neuron 1999; 24:585-593.
18. Yamashita, T., Higuchi, H., and Tohyama, M. The p75 receptor transduces the signal from myelin-associated glycoprotein to Rho. J Cell Biol 2002; 157:565-570.
19. Wang, K. C., Kim, J. A., Sivasankaran, R., Segal, R., and He, Z. P75 interacts with the Nogo receptor as a co-receptor for Nogo, MAG and OMgp. Nature 2002; 420:74-78.
20. Wong, S. T., Henley, J. R., Kanning, K. C., Huang, K. H., Bothwell, M., and Poo, M. M. A p75(NTR) and Nogo receptor complex mediates repulsive signaling by myelin-associated glycoprotein. Nat Neurosci 2002; 5:1302-1308.
21. Mi, S., Lee, X., Shao, Z., Thill, G., Ji, B., Relton, J., Levesque, M., Allaire, N., Perrin, S., Sands, B., Crowell, T., Cate, R. L., McCoy, J. M., and Pepinsky, R. B. LINGO1 is a component of the Nogo-66 receptor/p75 signaling complex. Nat Neurosci 2004; 7:221-228.
22. Lauren, J., Airaksinen, M. S., Saarma, M., and Timmusk, T. Two novel mammalian Nogo receptor homologs differentially expressed in the central and peripheral nervous systems. Mol Cell Neurosci 2003; 24:581-594.
23. Venkatesh, K., Chivatakarn, O., Lee, H., Joshi, P. S., Kantor, D. B., Newman, B. A., Mage, R., Rader, C., and Giger, R. J. The Nogo-66 receptor homolog NgR2 is a sialic acid-dependent receptor selective for myelin-associated glycoprotein. J Neurosci 2005; 25:808-822.
24. Shao, Z., Browning, J. L., Lee, X., Scott, M. L., Shulga-Morskaya, S., Allaire, N., Thill, G., Levesque, M., Sah, D., McCoy, J. M., Murray, B., Jung, V., Pepinsky, R. B., and Mi, S. TAJ/TROY, an orphan TNF receptor family member, binds Nogo-66 receptor 1 and regulates axonal regeneration. Neuron 2005; 45:353-359.
25. Park, J. B., Yiu, G., Kaneko, S., Wang, J., Chang, J., and He, Z. A TNF receptor family member, TROY, is a coreceptor with Nogo receptor in mediating the inhibitory activity of myelin inhibitors. Neuron 2005; 45:345-351.
26. Bigner, S. H. and Vogelstein, B. Cytogenetics and molecular genetics of malignant gliomas and medulloblastoma. Brain Pathol 1990; 1:12-18.
27. Chernova, O. B., Somerville, R. P., and Cowell, J. K. A novel gene, LGI1, from 10q24 is rearranged and downregulated in malignant brain tumors. Oncogene 1998; 17:2873-2881.
28. Krex, D., Hauses, M., Appelt, H., Mohr, B., Ehninger, G., Schackert, H. K., and Schackert, G. Physical and functional characterization of the human LGI1 gene and its possible role in glioma development. Acta Neuropathol (Berl) 2002; 103:255-266.
29. Kunapuli, P., Chitta, K. S., and Cowell, J. K. Suppression of the cell proliferation and invasion phenotypes in glioma cells by the LGI1 gene. Oncogene 2003; 22:3985-3991.
30. Gu, W., Brodtkorb, E., and Steinlein, O. K. LGI1 is mutated in familial temporal lobe epilepsy characterized by aphasic seizures. Ann Neurol 2002; 52:364-367.
31. Gu, W., Wevers, A., Schroder, H., Grzeschik, K. H., Derst, C., Brodtkorb, E., de Vos, R., and Steinlein, O. K. The LGI1 gene involved in lateral temporal lobe epilepsy belongs to a new subfamily of leucine-rich repeat proteins. FEBS Lett 2002; 519:71-76.
32. Morante-Redolat, J. M., Gorostidi-Pagola, A., Piquer-Sirerol, S., Saenz, A., Poza, J. J., Galan, J., Gesk, S., Sarafidou, T., Mautner, V. F., Binelli, S., Staub, E., Hinzmann, B., French, L., Prud'homme, J. F., Passarelli, D., Scannapieco, P., Tassinari, C. A., Avanzini, G., Marti-Masso, J. F., Kluwe, L., Deloukas, P., Moschonas, N. K., Michelucci, R., Siebert, R., Nobile, C., Perez-Tur, J., and Lopez de Munain, A. Mutations in the LGI1/Epitempin gene on 1024 cause autosomal dominant lateral temporal epilepsy. Hum Mol Genet 2002; 11:1119-1128.
33. Nakayama, J., Hamano, K., Iwasaki, N., Ohta, M., Nakahara, S., Matsui, A., and Arinami, T. Mutation analysis of the leucine-rich, glioma inactivated 1 gene (LGI1) in Japanese febrile seizure patients. Neuropediatrics 2003; 34:234-236.
34. Fertig, E., Lincoln, A., Martinuzzi, A., Mattson, R. H., and Hisama, F. M. Novel LGI1 mutation in a family with autosomal dominant partial epilepsy with auditory features. Neurology 2003; 60:1687-1690.
35. Bisulli, F., Tinuper, P., Scudellaro, E., Naldi, I., Bagattin, A., Avoni, P., Michelucci, R., and Nobile, C. A de novo LGI1 mutation in sporadic partial epilepsy with auditory features. Ann Neurol 2004; 56:455-456.
36. Ottman, R., Winawer, M. R., Kalachikov, S., Barker-Cummings, C., Gilliam, T. C., Pedley, T. A., and Hauser, W. A. LGI1 mutations in autosomal dominant partial epilepsy with auditory features. Neurology 2004; 62:1120-1126.
37. Berkovic, S. F., Izzillo, P., McMahon, J. M., Harkin, L. A., McIntosh, A. M., Phillips, H. A., Briellmann, R. S., Wallace, R. H., Mazarib, A., Neufeld, M. Y., Korczyn, A. D., Scheffer, I. E., and Mulley, J. C. LGI1 mutations in temporal lobe epilepsies. Neurology 2004; 62:1115-1119.
38. Hedera, P., Abou-Khalil, B., Crunk, A. E., Taylor, K. A., Haines, J. L., and Sutcliffe, J. S. Autosomal dominant lateral temporal epilepsy: two families with novel mutations in the LGI1 gene. Epilepsia 2004; 45:218-222.
39. Flex, E., Pizzuti, A., Di Bonaventura, C., Douzgou, S., Egeo, G., Fattouch, J., Manfredi, M., Dallapiccola, B., and Giallonardo, A. T. LGI1 gene mutation screening in sporadic partial epilepsy with auditory features. J Neurol 2005; 252:62-66.
40. Brodtkorb, E., Nakken, K. O., and Steinlein, O. K. No evidence for a seriously increased malignancy risk in LGI1-caused epilepsy. Epilepsy Res 2003; 56:205-208.
41. Staub, E., Perez-Tur, J., Siebert, R., Nobile, C., Moschonas, N. K., Deloukas, P., and Hinzmann, B. The novel EPTP repeat defines a superfamily of proteins implicated in epileptic disorders. Trends Biochem Sci 2002; 27:441-444.
42. Scheel, H., Tomiuk, S., and Hofmann, K. A common protein interaction domain links two recently identified epilepsy genes. Hum Mol Genet 2002; 11:1757-1762.
43. Nakashiba, T., Ikeda, T., Nishimura, S., Tashiro, K., Honjo, T., Culotti, J. G., and Itohara, S. Netrin-G1: a novel glycosyl phosphatidylinositol-linked mammalian netrin that is functionally divergent from classical netrins. J Neurosci 2000; 20:6540-6550.
44. Wong, K., Park, H. T., Wu, J. Y., and Rao, Y. Slit proteins: molecular guidance cues for cells ranging from neurons to leukocytes. Curr Opin Genet Dev 2002; 12:583-591.
45. Igarashi, M., Strittmatter, S. M., Vartanian, T., and Fishman, M. C. Mediation by G proteins of signals that cause collapse of growth cones. Science 1993; 259:77-79.
46. Luo, Y., Raible, D., and Raper, J. A. Collapsin: a protein in brain that induces the collapse and paralysis of neuronal growth cones. Cell 1993; 75:217-227.
47. Sicotte, M., Tsatas, O., Jeong, S. Y., Cai, C. Q., He, Z., and David, S. Immunization with myelin or recombinant Nogo-66/MAG in alum promotes axon regeneration and sprouting after corticospinal tract lesions in the spinal cord. Mol Cell Neurosci 2003; 23:251-263.
48. Dergham, P., Ellezam, B., Essagian, C., Avedissian, H., Lubell, W. D., and McKerracher, L. Rho signaling pathway targeted to promote spinal cord repair. J Neurosci 2002; 22:6570-6577.
49. Basso, D. M. Behavioral testing after spinal cord injury: congruities, complexities, and controversies. J Neurotrauma 2004; 21:395-404.
50. Martushova, K., Hisama, F. M., McGee, A. W., and Strittmatter, S. M. Characterization of secreted LGI1 in neuronal form and function. In: Annual Meeting of the Society for Neuroscience, San Diego, Calif., 2004.
51. Rabchevsky, A. G. and Smith, G. M. Therapeutic interventions following mammalian spinal cord injury. Arch Neurol 2001; 58:721-726.
52. Frohman, E. M., et al., *Therapeutic considerations for disease progression in multiple sclerosis: evidence, experience, and future expectations.* Arch Neurol, 2005. 62(10): p. 1519-30.
53. Zhao, C., et al., *Mechanisms of CNS remyelination—the key to therapeutic advances.* J Neurol Sci, 2005. 233(1-2): p. 87-91.

54. Dawson, M. R., et al., *NG2-expressing glial progenitor cells: an abundant and widespread population of cycling cells in the adult rat CNS.* Mol Cell Neurosci, 2003. 24(2): p. 476-88.
55. Gensert, J. M. and J. E. Goldman, *Endogenous progenitors remyelinate demyelinated axons in the adult CNS.* Neuron, 1997. 19(1): p. 197-203.
56. Keirstead, H. S. and W. F. Blakemore, *Identification of post-mitotic oligodendrocytes incapable of remyelination within the demyelinated adult spinal cord.* J Neuropathol Exp Neurol, 1997. 56(11): p. 1191-201.
57. Watanabe, M., Y. Toyama, and A. Nishiyama, *Differentiation of proliferated NG2-positive glial progenitor cells in a remyelinating lesion.* J Neurosci Res, 2002. 69(6): p. 826-36.
58. Levine, J. M. and R. Reynolds, *Activation and proliferation of endogenous oligodendrocyte precursor cells during ethidium bromide-induced demyelination.* Exp Neurol, 1999. 160(2): p. 33347.
59. Redwine, J. M. and R. C. Armstrong, *In vivo proliferation of oligodendrocyte progenitors expressing PDGFalphaR during early remyelination.* J Neurobiol, 1998. 37(3): p. 413-28.
60. Penderis, J., S. A. Shields, and R. J. Franklin, *Impaired remyelination and depletion of oligodendrocyte progenitors does not occur following repeated episodes of focal demyelination in the rat central nervous system.* Brain, 2003. 126(Pt 6): p. 1382-91.
61. Bermingham, J. R., et al., *The claw paw mutation reveals a role for Lgi4 in peripheral nerve development.* Nat Neurosci, 2005.
62. Mi, S., et al., *LINGO1 negatively regulates myelination by oligodendrocytes.* Nat Neurosci, 2005. 8(6): p. 745-51.
63. Cosgaya, J. M., J. R. Chan, and E. M. Shooter, *The neurotrophin receptor p75NTR as a positive modulator of myelination.* Science, 2002. 298(5596): p. 1245-8.
64. Song, X.Y., et al., *Knockout of p75 impairs re-myelination of injured sciatic nerve in mice.* J Neurochem, 2005.

What is claimed is:

1. A method of promoting axonal regrowth of neurons after injury to the central nervous system in a subject, comprising administration of an effective amount of a leucine-rich, glioma-inactivated protein, wherein the leucine-rich, glioma-inactivated protein is LGI1, to the site of the injury in the subject.

2. A method of promoting axonal regrowth of neurons after injury to the central nervous system in a subject, comprising administration of an effective amount of a leucine-rich, glioma-inactivated protein, wherein the leucine-rich, glioma-inactivated protein is LGI1, to the site of the injury in the subject, wherein myelin-based axon growth inhibitor (MBGI) receptor activation is blocked, thereby promoting axonal regrowth of neurons after injury to the central nervous system.

3. A method of promoting axonal regrowth of neurons after injury to the central or peripheral nervous system in a subject, comprising administration of an effective amount of a leucine-rich, glioma-inactivated protein, wherein the leucine-rich, glioma-inactivated protein is LGI1, to the site of the injury in the subject.

4. A method of promoting axonal regrowth of neurons after injury to the peripheral nervous system in a subject, comprising administration of an effective amount of a leucine-rich, glioma-inactivated protein, wherein the leucine-rich, glioma-inactivated protein is LGI1, to the site of the injury in the subject.

5. A method of treating central or peripheral nerve damage comprising the administration of an effective amount of a leucine-rich, glioma-inactivated protein, wherein the leucine-rich, glioma-inactivated protein is LGI1, to the site of the damage.

* * * * *

SEQUENCE LISTING

```
<160> NUMBER OF SEQ ID NOS: 3

<210> SEQ ID NO 1
<211> LENGTH: 557
<212> TYPE: PRT
<213> ORGANISM: Mouse

<400> SEQUENCE: 1

Met Glu Ser Glu Ser Ser Arg Arg Met Gly Asn Ala Cys Ile Pro Leu
1               5                   10                  15

Lys Arg Ile Ala Tyr Phe Leu Cys Leu Phe Ser Val Val Leu Leu Thr
            20                  25                  30

Glu Gly Lys Lys Pro Ala Lys Pro Lys Cys Pro Ala Val Cys Thr Cys
        35                  40                  45

Ser Lys Asp Asn Ala Leu Cys Glu Asn Ala Arg Ser Ile Pro Arg Thr
    50                  55                  60

Val Pro Pro Asp Val Ile Ser Leu Ser Phe Val Arg Ser Gly Phe Thr
65                  70                  75                  80

Glu Ile Ser Glu Gly Ser Phe Leu Phe Thr Pro Ser Leu Gln Leu Leu
                85                  90                  95

Leu Phe Thr Ser Asn Ser Phe Asp Val Ile Ser Asp Asp Ala Phe Ile
            100                 105                 110

Gly Leu Pro His Leu Glu Tyr Leu Phe Ile Glu Asn Asn Asn Ile Lys
        115                 120                 125

Ser Ile Ser Arg His Thr Phe Arg Gly Leu Lys Ser Leu Ile His Leu
    130                 135                 140

Ser Leu Ala Asn Asn Asn Leu Gln Thr Leu Pro Lys Asp Ile Phe Lys
145                 150                 155                 160

Gly Leu Asp Ser Leu Thr Asn Val Asp Leu Arg Gly Asn Ala Phe Asn
                165                 170                 175

Cys Asp Cys Lys Leu Lys Trp Leu Val Glu Trp Leu Gly His Thr Asn
            180                 185                 190

Ala Thr Val Glu Asp Ile Tyr Cys Glu Gly Pro Pro Glu Tyr Lys Lys
        195                 200                 205

Arg Lys Ile Asn Ser Leu Ser Pro Lys Asp Phe Asp Cys Ile Ile Thr
    210                 215                 220

Glu Phe Ala Lys Ser Gln Asp Leu Pro Tyr Gln Ser Leu Ser Ile Asp
```

```
                225                 230                 235                 240
Thr Phe Ser Tyr Leu Asn Asp Glu Tyr Val Val Ile Ala Gln Pro Phe
                245                 250                 255

Thr Gly Lys Cys Ile Phe Leu Glu Trp Asp His Val Glu Lys Thr Phe
            260                 265                 270

Arg Asn Tyr Asp Asn Ile Thr Gly Thr Ser Thr Val Cys Lys Pro
        275                 280                 285

Ile Val Ile Asp Thr Gln Leu Tyr Val Ile Val Ala Gln Leu Phe Gly
    290                 295                 300

Gly Ser His Ile Tyr Lys Arg Asp Gly Phe Ala Asn Lys Phe Ile Lys
305                 310                 315                 320

Ile Gln Asp Ile Glu Val Leu Lys Ile Arg Lys Pro Asn Asp Ile Glu
                325                 330                 335

Thr Phe Lys Ile Glu Asp Asn Trp Tyr Phe Val Val Ala Asp Ser Ser
            340                 345                 350

Lys Ala Gly Phe Thr Thr Ile Tyr Lys Trp Asn Gly Asn Gly Phe Tyr
        355                 360                 365

Ser His Gln Ser Leu His Ala Trp Tyr Arg Asp Thr Asp Val Glu Tyr
    370                 375                 380

Leu Glu Ile Ala Arg Pro Pro Leu Ala Leu Arg Thr Pro His Leu Ile
385                 390                 395                 400

Leu Ser Ser Ser Gln Arg Pro Val Ile Tyr Gln Trp Ser Lys Ala
                405                 410                 415

Thr Gln Leu Phe Thr Asn Gln Thr Asp Ile Pro Asn Met Glu Asp Val
            420                 425                 430

Tyr Ala Val Lys His Phe Ser Val Lys Gly Asp Val Tyr Ile Cys Leu
        435                 440                 445

Thr Arg Phe Ile Gly Asp Ser Lys Val Met Lys Trp Gly Gly Ser Ser
    450                 455                 460

Phe Gln Asp Ile Gln Arg Met Pro Ser Arg Gly Ser Met Val Phe Gln
465                 470                 475                 480

Pro Leu Gln Ile Asn Asn Tyr Gln Tyr Ala Ile Leu Gly Ser Asp Tyr
                485                 490                 495

Ser Phe Thr Gln Val Tyr Asn Trp Asp Ala Glu Lys Ala Lys Phe Val
            500                 505                 510

Lys Phe Gln Glu Leu Asn Val Gln Ala Pro Arg Ser Phe Thr His Val
        515                 520                 525

Ser Ile Asn Lys Arg Asn Phe Leu Phe Ala Ser Ser Phe Lys Gly Asn
    530                 535                 540

Thr Gln Ile Tyr Lys His Val Ile Val Asp Leu Ser Ala
545                 550                 555

<210> SEQ ID NO 2
<211> LENGTH: 557
<212> TYPE: PRT
<213> ORGANISM: Rat

<400> SEQUENCE: 2

Met Glu Ser Glu Ser Ile Arg Arg Met Gly Asn Ala Cys Ile Pro Leu
1               5                   10                  15

Lys Arg Ile Ala Tyr Phe Leu Cys Leu Phe Ser Val Val Leu Leu Thr
            20                  25                  30

Glu Gly Lys Lys Pro Ala Lys Pro Lys Cys Pro Ala Val Cys Thr Cys
        35                  40                  45

Ser Lys Asp Asn Ala Leu Cys Glu Asn Ala Arg Ser Ile Pro Arg Thr
```

```
                50                  55                  60
Val Pro Pro Asp Val Ile Ser Leu Ser Phe Val Arg Ser Gly Phe Thr
65                  70                  75                  80

Glu Ile Ser Glu Gly Ser Phe Leu Phe Thr Pro Ser Leu Gln Leu Leu
                85                  90                  95

Leu Phe Thr Ser Asn Ser Phe Asp Val Ile Ser Asp Asp Ala Phe Ile
                100                 105                 110

Gly Leu Pro His Leu Glu Tyr Leu Phe Ile Glu Asn Asn Asn Ile Lys
                115                 120                 125

Ser Ile Ser Arg His Thr Phe Arg Gly Leu Lys Ser Leu Ile His Leu
130                 135                 140

Ser Leu Ala Asn Asn Asn Leu Gln Thr Leu Pro Lys Asp Ile Phe Lys
145                 150                 155                 160

Gly Leu Asp Ser Leu Thr Asn Val Asp Leu Arg Gly Asn Ser Phe Asn
                165                 170                 175

Cys Asp Cys Lys Leu Lys Trp Leu Val Glu Trp Leu Gly His Thr Asn
                180                 185                 190

Ala Thr Val Glu Asp Ile Tyr Cys Glu Gly Pro Pro Glu Tyr Lys Lys
                195                 200                 205

Arg Lys Ile Asn Ser Leu Ser Pro Lys Asp Phe Asp Cys Ile Ile Thr
210                 215                 220

Glu Phe Ala Lys Ser Gln Asp Leu Pro Tyr Gln Ser Leu Ser Ile Asp
225                 230                 235                 240

Thr Phe Ser Tyr Leu Asn Asp Glu Tyr Val Val Ile Ala Gln Pro Phe
                245                 250                 255

Thr Gly Lys Cys Ile Phe Leu Glu Trp Asp His Val Glu Lys Thr Phe
                260                 265                 270

Arg Asn Tyr Asp Asn Ile Thr Gly Thr Ser Thr Val Cys Lys Pro
                275                 280                 285

Ile Val Ile Asp Thr Gln Leu Tyr Val Ile Val Ala Gln Leu Phe Gly
290                 295                 300

Gly Ser His Ile Tyr Lys Arg Asp Gly Phe Ala Asn Lys Phe Ile Lys
305                 310                 315                 320

Ile Gln Asp Ile Glu Val Leu Lys Ile Arg Lys Pro Asn Asp Ile Glu
                325                 330                 335

Thr Phe Lys Ile Glu Asp Asn Trp Tyr Phe Val Val Ala Asp Ser Ser
                340                 345                 350

Lys Ala Gly Phe Thr Thr Ile Tyr Lys Trp Asn Gly Asn Gly Phe Tyr
                355                 360                 365

Ser His Gln Ser Leu His Ala Trp Tyr Arg Asp Thr Asp Val Glu Tyr
370                 375                 380

Leu Glu Ile Ala Arg Pro Pro Leu Thr Leu Arg Thr Pro His Leu Ile
385                 390                 395                 400

Leu Ser Ser Ser Ser Gln Arg Pro Val Ile Tyr Gln Trp Ser Lys Ala
                405                 410                 415

Thr Gln Leu Phe Ile Asn Gln Thr Asp Ile Pro Asn Met Glu Asp Val
                420                 425                 430

Tyr Ala Val Lys His Phe Ser Val Lys Gly Asp Val Tyr Ile Cys Leu
                435                 440                 445

Thr Arg Phe Ile Gly Asp Ser Lys Val Met Lys Trp Gly Gly Ser Ser
450                 455                 460

Phe Gln Asp Ile Gln Arg Met Pro Ser Arg Gly Ser Met Val Phe Gln
465                 470                 475                 480
```

-continued

```
Pro Leu Gln Ile Asn Asn Tyr Gln Tyr Ala Ile Leu Gly Ser Asp Tyr
            485                 490                 495

Ser Phe Thr Gln Val Tyr Asn Trp Asp Ala Glu Lys Ala Lys Phe Val
                500                 505                 510

Lys Phe Gln Glu Leu Asn Val Gln Ala Pro Arg Ser Phe Thr His Val
            515                 520                 525

Ser Ile Asn Lys Arg Asn Phe Leu Phe Ala Ser Ser Phe Lys Gly Asn
530                 535                 540

Thr Gln Ile Tyr Lys His Val Ile Val Asp Leu Ser Ala
545                 550                 555

<210> SEQ ID NO 3
<211> LENGTH: 557
<212> TYPE: PRT
<213> ORGANISM: Human

<400> SEQUENCE: 3

Met Glu Ser Glu Arg Ser Lys Arg Met Gly Asn Ala Cys Ile Pro Leu
1               5                   10                  15

Lys Arg Ile Ala Tyr Phe Leu Cys Leu Leu Ser Ala Leu Leu Leu Thr
                20                  25                  30

Glu Gly Lys Lys Pro Ala Lys Pro Lys Cys Pro Ala Val Cys Thr Cys
            35                  40                  45

Thr Lys Asp Asn Ala Leu Cys Glu Asn Ala Arg Ser Ile Pro Arg Thr
        50                  55                  60

Val Pro Pro Asp Val Ile Ser Leu Ser Phe Val Arg Ser Gly Phe Thr
65                  70                  75                  80

Glu Ile Ser Glu Gly Ser Phe Leu Phe Thr Pro Ser Leu Gln Leu Leu
                85                  90                  95

Leu Phe Thr Ser Asn Ser Phe Asp Val Ile Ser Asp Asp Ala Phe Ile
            100                 105                 110

Gly Leu Pro His Leu Glu Tyr Leu Phe Ile Glu Asn Asn Asn Ile Lys
        115                 120                 125

Ser Ile Ser Arg His Thr Phe Arg Gly Leu Lys Ser Leu Ile His Leu
130                 135                 140

Ser Leu Ala Asn Asn Asn Leu Gln Thr Leu Pro Lys Asp Ile Phe Lys
145                 150                 155                 160

Gly Leu Asp Ser Leu Thr Asn Val Asp Leu Arg Gly Asn Ser Phe Asn
                165                 170                 175

Cys Asp Cys Lys Leu Lys Trp Leu Val Glu Trp Leu Gly His Thr Asn
            180                 185                 190

Ala Thr Val Glu Asp Ile Tyr Cys Glu Gly Pro Pro Glu Tyr Lys Lys
        195                 200                 205

Arg Lys Ile Asn Ser Leu Ser Ser Lys Asp Phe Asp Cys Ile Ile Thr
210                 215                 220

Glu Phe Ala Lys Ser Gln Asp Leu Pro Tyr Gln Ser Leu Ser Ile Asp
225                 230                 235                 240

Thr Phe Ser Tyr Leu Asn Asp Glu Tyr Val Val Ile Ala Gln Pro Phe
                245                 250                 255

Thr Gly Lys Cys Ile Phe Leu Glu Trp Asp His Val Glu Lys Thr Phe
            260                 265                 270

Arg Asn Tyr Asp Asn Ile Thr Gly Thr Ser Thr Val Val Cys Lys Pro
        275                 280                 285

Ile Val Ile Glu Thr Gln Leu Tyr Val Ile Val Ala Gln Leu Phe Gly
290                 295                 300
```

-continued

```
Gly Ser His Ile Tyr Lys Arg Asp Ser Phe Ala Asn Lys Phe Ile Lys
305                 310                 315                 320

Ile Gln Asp Ile Glu Ile Leu Lys Ile Arg Lys Pro Asn Asp Ile Glu
                325                 330                 335

Thr Phe Lys Ile Glu Asn Asn Trp Tyr Phe Val Val Ala Asp Ser Ser
            340                 345                 350

Lys Ala Gly Phe Thr Thr Ile Tyr Lys Trp Asn Gly Asn Gly Phe Tyr
        355                 360                 365

Ser His Gln Ser Leu His Ala Trp Tyr Arg Asp Thr Asp Val Glu Tyr
    370                 375                 380

Leu Glu Ile Val Arg Thr Pro Gln Thr Leu Arg Thr Pro His Leu Ile
385                 390                 395                 400

Leu Ser Ser Ser Ser Gln Arg Pro Val Ile Tyr Gln Trp Asn Lys Ala
                405                 410                 415

Thr Gln Leu Phe Thr Asn Gln Thr Asp Ile Pro Asn Met Glu Asp Val
            420                 425                 430

Tyr Ala Val Lys His Phe Ser Val Lys Gly Asp Val Tyr Ile Cys Leu
        435                 440                 445

Thr Arg Phe Ile Gly Asp Ser Lys Val Met Lys Trp Gly Gly Ser Ser
    450                 455                 460

Phe Gln Asp Ile Gln Arg Met Pro Ser Arg Gly Ser Met Val Phe Gln
465                 470                 475                 480

Pro Leu Gln Ile Asn Asn Tyr Gln Tyr Ala Ile Leu Gly Ser Asp Tyr
                485                 490                 495

Ser Phe Thr Gln Val Tyr Asn Trp Asp Ala Glu Lys Ala Lys Phe Val
            500                 505                 510

Lys Phe Gln Glu Leu Asn Val Gln Ala Pro Arg Ser Phe Thr His Val
        515                 520                 525

Ser Ile Asn Lys Arg Asn Phe Leu Phe Ala Ser Ser Phe Lys Gly Asn
    530                 535                 540

Thr Gln Ile Tyr Lys His Val Ile Val Asp Leu Ser Ala
545                 550                 555
```